United States Patent [19]

Di Pardo et al.

[11] Patent Number: 4,535,164

[45] Date of Patent: Aug. 13, 1985

[54] PROCESS FOR PREPARING CERTAIN SUBSTITUTED 4-THIAZOLIDINONES

[75] Inventors: Robert M. Di Pardo, Lansdale; Mark G. Bock, Hatfield, both of Pa.

[73] Assignee: Merck & Co., Inc., Rahway, N.J.

[21] Appl. No.: 478,272

[22] Filed: Mar. 30, 1983

Related U.S. Application Data

[63] Continuation-in-part of Ser. No. 312,607, Oct. 19, 1981, abandoned.

[51] Int. Cl.$^3$ ............................................. C07D 277/34
[52] U.S. Cl. ...................................................... 548/187
[58] Field of Search .......................................... 548/187

[56] References Cited

U.S. PATENT DOCUMENTS 4,225,609  9/1980  Cragoe et al. ...................... 548/187

OTHER PUBLICATIONS

Surrey et al, J. Am. Chem. Soc. 69, 2911, (1947).
Erlenmeyer, Helv. Chim. Acta 30, 1329, (1947).
Rout et al, J. Am. Chem. Soc. 77, 2427, (1955).
Pacha et al, Helv. Chim. Acta, 39, 1156, (1956).
Di Pardo et al, Synthesis, 10, 825, (1981).
Kametani et al, Heterocycles 9, 831, (1978).
Ishidate, J. Pharm. Soc. Japan, 76, 73, (1956).

Primary Examiner—Robert Gerstl
Attorney, Agent, or Firm—Daniel T. Szura; Salvatore C. Mitri

[57] ABSTRACT

A process is disclosed for preparing 4-thiazolidinones having the formula:

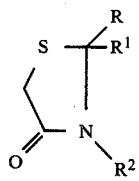

by cyclizing a compound of the formula:

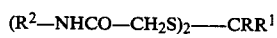

in an aprotic reaction medium in the presence of a metal catalyst.

5 Claims, No Drawings

PROCESS FOR PREPARING CERTAIN SUBSTITUTED 4-THIAZOLIDINONES

BACKGROUND OF THE INVENTION

This application is a continuation-in-part of application Ser. No. 312,607 filed Oct. 19, 1981 now abandoned.

The subject matter of the present invention relates to the preparation of certain substituted 4-thiazolidinones. These thiazolidinones are useful as pharmaceuticals, biologicals, chemical intermediates etc.

Processes for preparing 4-thiazolidinones are described in the literature; see e.g., A. R. Surrey, J.A.C.S. 69, 2911 (1947) and 76, 578 (1954); H. Erlenmeyer et al., Helv. Chim. Acta 30, 1329 (1947); M. K. Rout et al., J.A.C.S., 77, 2427 (1955); W. Pacha et al., Helv. Chim. Acta 39, 1156 (1956) and M. Ishidate et al., J. Pharm. Soc. Japan 76, 73 (1956), U.S. Pat. No. 4,225,609. These processes generally require harsh reaction conditions. In some instances, even these harsh process conditions fail to yield the desired 4-thiazolidinone; see T. Kametani et al., Heterocycles 9, 831 (1978).

A process for preparing certain 4-thiazolidinones using mild and operationally simple conditions which permits the reaction to go to completion has been discovered.

SUMMARY OF THE INVENTION

A process for preparing 4-thiazolidinones of the formula:

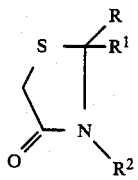

by cyclizing a compound of the formula:

$$(R^2NHCO-CH_2-S)_2CRR^1$$

in an aprotic reaction medium in the presence of a metal catalyst.

DETAILED DESCRIPTION OF THE INVENTION

An embodiment of the present invention is a process for preparing compounds of the formula:

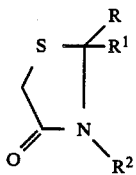

wherein

R and $R^1$, are independently H; $C_1$-$C_8$ alkyl; phenyl; or $-(CH_2)_n-AR^3$ wherein:

$R^3$ is carboxy, a carboxy salt, a carboxy ester of the formula $COOR^5$ wherein $R^5$ is $C_{1-10}$ alkyl;

A is p-phenylene, m-phenylene or subsituted phenylene derivative in which one or two of the phenylene hydrogens is replaced by methyl, halo, or 2,5-furylene; and n is 3 or 4;

and $R_2$ is

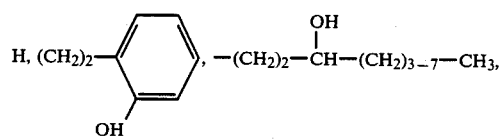

phenyl, phen-$C_1$-$C_8$-alkyl or

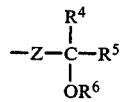

wherein:

Z is alkylene or unsaturated alkylene having from 2–3 carbon atoms;

$R^6$ is hydrogen or lower alkanoyl;

$R^5$ is hydrogen or straight chain $C_{1-3}$ alkyl; and $R^4$ is lower straight chain or branched alkyl having from 3–7 carbon atoms, an unsaturated alkyl having from 3–7 carbon atoms, or a substituted lower alkyl selected from polyfluoro alkyl of from 3–7 carbon atoms and lower alkoxy methylene; or $R^4$ and $R^5$ taken together with the carbon atom connecting $R^4$ and $R^5$ is a cyclic substituent selected from a bridged or unbridged alicyclic ring of from 5–9 carbon atoms or a heterocyclic ring containing oxygen and from 5–7 ring-forming carbon atoms such that at least one of R, $R^1$ and $R^2$ is other than H, which comprises cyclizing a compound of the formula:

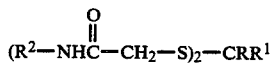

in an aprotic reaction medium in the presence of a Group I or Group II metal catalyst.

The thiazolidinones prepared by the present process are useful as intermediates, pharmaceuticals, biologicals and the like.

Any aprotic reaction medium may be used. Examples of such media are, hexamethylphosphoramide, tetrahydrofuran, tetramethylurea acetonitrile, methylene chloride and the like. Acetonitrile is a preferred medium.

The metal catalyst is general prouded as a metal salt. The salts of Group I or II metals such as silver, mercury and the like are useful. The mercury salts are more preferred. The mercuric salts such as $HgCl_2$, mercuric acetate and the like are most preferred. The amount of catalyst used may be varied a useful range is from about 1 to 8 equivalents of metal preferably from 2 to 5 equivalents.

The process is generally carried out at or about room temperature. Higher temperatures may be used, if desired.

The process is illustrated by the following reaction equation

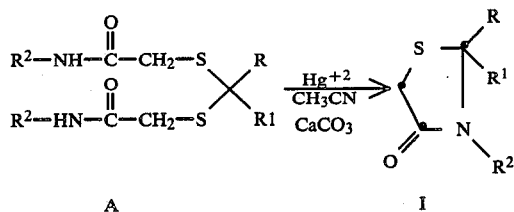

Methods for preparing the thioketal/thioacetal starting materials; i.e., the formula A compounds [R²—CH-CO—CH₂—S)₂CRR¹], are well established in the literature and known to those skilled in the art. The following reaction sequence illustrates the preparation of the formula A compound wherein R, R¹, and R² are as defined above:

Step 1

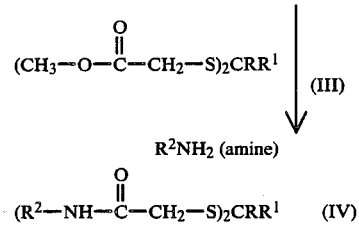

Step 2

Boron trifluoride etherate

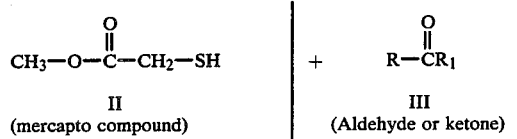

As shown in the foregoing reaction sequence, the Step 1 reaction provides coupling of a mercapto compound (II) with an aldehyde or ketone (III) to form a thio ketal/acetal (III) and is well known [see; e.g., *Organic Chemistry*, Allinger et al., Worth Pub., New York, N.Y., (1971), pp 478–479; Voronkina et al., *Zb. Obsch Khimii*, 32, 3804–3808, (1962)].

Preparation of an amide (IV) from the corresponding ester (III) as shown in Step 2 is also well known [see; e.g., *Organic Chemistry*, pp. 530–531].

The methyl glycolate is a known compound (see Aldrich Catalog, pg. 672) as are the R²NH₂ amines and the RR¹C=O ketones or aldehydes.

The Step 1 and Step 2 reaction sequence preparations are further illustrated by the following Preparations.

Preparation 1

Step 1
 +

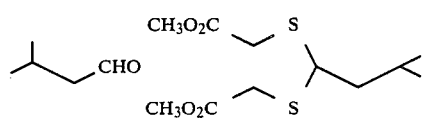

PREPARATION OF THE THIOACETAL OF ISO-VALERALDEHYDE

A magnetically stirred solution of 20.22 g (0.2347 mole) of i-valeraldehyde in 150 ml of dry methylene chloride containing 20 ml (0.1626 mole) of boron trifluoride etherate is treated dropwise with 42 ml (0.4695 mole) of methylthioglycolate. The reaction is slightly exothermic; the reaction temperature is moderated by the application of a cold water bath. After addition is complete (@½ hour) the reaction mixture is protected from moisture and allowed to stand at room temperature for 12 hours. The reaction mixture is then poured into 200 ml of water and the phases separated. The organic phase is washed in succession with 10% sodium hydroxide solution (3×100 ml), 10% sodium bisulfite solution (3×100 ml) and brine. Rotoevaporation of the dried (MgSO₄) extracts affords 34 g of a yellow oil which is distilled at 135°–136° C./0.45 Torr through a 10 cm Vigreux column. In this way, 25 g of product is obtained.

ir (CHCl₃, partial): No SH stretch, 1730, 1435, 1290, 1160, 1005 cm⁻¹.

Pmr (CDCl₃): 0.9 (6H, d, J 6.5), 1.7 (3H, m), 3.33 (2H, s), 3.4 (2H, s), 3.7 (6H, s), 4.1 (1H, m).

Preparation 2

Step 2

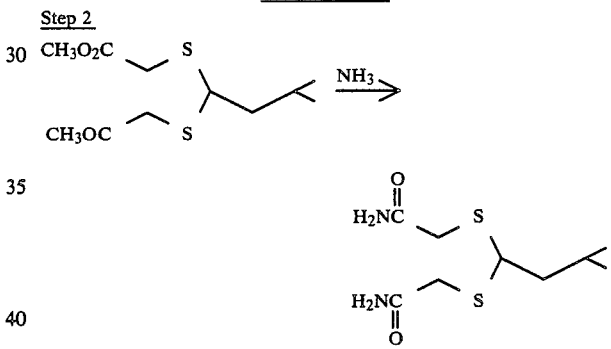

PREPARATION OF THE THIOACETAL-AMIDE OF ISO-VALERALDEHYDE

Ammonia gas is passed continuously into a stirred solution of 100 ml of dry methanol containing 100 mg (1.78 mmole) of sodium methoxide and 5.0 g (17.84 mmole) of the i-valeraldehydethioacetal. After 5 hours, excess ammonia and the solvent are removed under reduced pressure to give an oil which solidifies on standing. Two recrystallizations from ethyl acetate and treatment with norite give the analytically pure product as white, feathery needles, mp 95.5°–96.5° C. R*f*=0.37 (9:1 methylene chloride/methanol)

ir (KBr, partial): 3375, 3180, 1650, 1380 cm⁻¹.

Pmr (DMSO-d₆): 0.85 (6H, d, J~6), 1.55 (2H, m), 1.8 (1H, hept, j 6), 3.18 (4H, s), 4.13 (1H, t, J 9), 7.0 (2H, b.s., NH₂), 7.4 (2H, b.s., NH₂).

The following general procedure illustrates the process of the invention.

GENERAL PROCEDURE

A compound of the formula A (5 mmol) in 50 ml of dry acetonitrile is treated with mercuric chloride (20 mmol) and calcium carbonate (20 mmol). The resulting mixture is protected from moisture and stirred at ambient (room) temperature. The reaction is monitored by TLC (thin layer chromatography) and is usually complete in a few hours. The product is recovered via a work-up which consists of filtration in one of two ways, as follows:

RECOVERY METHOD A

The solvent (acetonitrile) is removed (e.g. vacuum) and the residue is partitioned between ethyl acetate and water. The organic phase is washed with sodium sulfite solution, dried and concentrated to yield the formula I product.

RECOVERY METHOD B

The solvent is removed (e.g. vacuum) and the residue is dissolved in ethyl acetate. Hydrogen sulfide gas is passed into the solution until precipitation is complete. The mixture is then rendered neutral with $NH_3$ and filtered. The solvent is removed from the filtrate by rotoevaporation to yield the formula I product. Analytical samples are obtained after distillation or recrystallization from an appropriate solvent.

Using appropriate formula A starting materials, and the procedure described above the following tabulated compounds were prepared.

TABLE 1
COMPOUNDS OF THE FORMULA

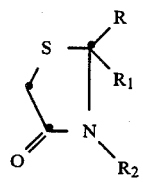

| EXAMPLE | R | $R_1$ | $R_2$ | Yield[a] [%] | m.p. [°C.][b] (Solvent) | Molecular Formula[c] | I.R. (KBr) ν [cm$^{-1}$] | $^1$H—N.M.R. (CDCl$_3$/Me$_4$Si) [ppm] |
|---|---|---|---|---|---|---|---|---|
| 1 | phenyl | H | H | 58 | 127–129° (methanol) | C$_9$H$_9$NOS (179.24) | 3150, 3050, 1670 | 3.61 (1H, s), 3.63 (1H, s), 5.75 (1H, bs), 7.18 (1H, bs, NH), 7.33 (5H, s, arom). |
| 2 | —(CH$_2$)$_4$—CH$_3$ | H | H | 40 | 60–61° (pet. ether) | C$_8$H$_{15}$NOS (173.28) | 3150, 3060, 1675 | 0.90 (3H, m, CH$_3$), 1.30 (8H, m), 3.48 (1H, s) 3.51 (1H, s), 4.68 (1H, t, J=6), 7.9 (1H, bs, NH). |
| 3 | —CH$_2$CH(CH$_3$)$_2$ | H | H | 68 | 66–68° (ether/pet. ether) | C$_7$H$_{13}$NOS (159.17) | 3160, 3060, 1680. | 0.83 (3H, d, J=3), 0.90 (3H, d, J=3), 1.60 (3H, m), 3.77 (2H, s), 4.67 (1H, m), 8.60 (1H, bs, NH). |
| 4 | —(CH$_2$)$_3$-phenyl-CO$_2$Et | H | H | 43 | 98–99° (i-propanol) | C$_{15}$H$_{19}$NO$_3$S (293.39) | 3150, 1707, 1677, 1270 | 1.38 (3H, t, J=7), 1.78 (4H, m), 2.68 (2H, m, benzyl), 3.48 (2H, s), 4.33 (2H, q, J=7), 4.70 (1H, m), 7.22 (2H, d, J=7), 7.88 (1H, bs, NH). 7.93 (2H, d, J=7). |
| 5 | phenyl | H | phenyl-CH$_2$— | 29 | 151–153° (methanol) | C$_{16}$H$_{15}$NOS (269.37) | 3025, 1650, 1400 | 3.52 (1H, d, J=15, benzyl), 3.78 (2H, bs), 5.12 (1H, d, J=15, benzyl), 5.37 (1H, s), 7.3 (5H, m, arom). |
| 6 | —CH$_2$CH(CH$_3$)$_2$ | H | phenyl-CH—CH$_3$ | 0 | — | — | — | — |
| 7 | CH$_3$ | CH$_3$ | H | 28 | 125–126° (ether/pet. | C$_5$H$_9$NOS (131.19) | 3150, 1700, 1660, | 1.68 (6H, s), 3.65 (2H, s), 8.4 (1H, bs, NH). |

TABLE 1-continued

COMPOUNDS OF THE FORMULA

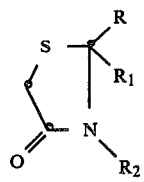

| EX-AM-PLE | R | R₁ | R₂ | Yield$^a$ [%] | m.p. [°C.]$^b$ (Solvent) | Molecular Formula$^c$ | I.R. (KBr) ν [cm$^{-1}$] | $^1$H—N.M.R. (CDCl$_3$/Me$_4$Si) [ppm] |
|---|---|---|---|---|---|---|---|---|
| | | | | | ether) | | 800 | |

$^a$Yield of recrystallized products; not optimized.
$^b$Uncorrected.
$^c$The microanalytical data showed the following maximal deviations from the theoretical values: N, ±0.22; C, ±0.18, H, ±0.11.

Claims to the invention follow:
What is claimed is:
1. A process for preparing compounds of the formula:

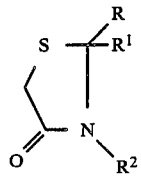

wherein
R and R₁ are independently H; or C₁-C₈ alkyl; phenyl; or —(CH₂)$_n$—A—R³ wherein:
R³ is carboxy, a carboxy salt, a carboxy ester of the formula COOR⁵ wherein R⁵ is C$_{1-10}$ alkyl;
A is p-phenylene, m-phenylene or subsituted phenylene derivative in which one or two of the phenylene hydrogens is replaced by methyl, halo, or 2,5-furylene; and
n is 3 or 4;
and
R² is

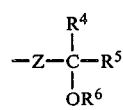

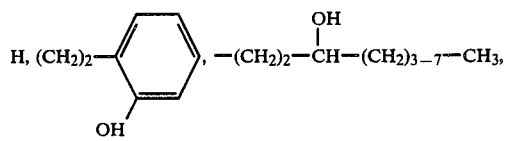

phenyl, phen-C₁-C₈-straight chain alkyl or

—Z—C(R⁴)(R⁵)—OR⁶ wherein:
Z is alkylene or unsaturated alkylene having from 2-3 carbon atoms;
R⁶ is hydrogen or lower alkanoyl;
R⁵ is hydrogen or straight chain C$_{1-3}$ alkyl; and
R⁴ is lower straight chain or branched alkyl having from 3-7 carbon atoms, an unsaturated alkyl having from 3-7 carbon atoms, or a substituted lower alkyl selected from polyfluoro alkyl of from 3-7 carbon atoms and lower alkoxy methylene; or R⁴ and R⁵ taken together with the carbon atom connecting R⁴ and R⁵ is a cyclic substituent selected from a bridged or unbridged alicyclic ring of from 5-9 carbon atoms or a heterocyclic ring containing oxygen and from 5-7 ring-forming carbon atoms such that at least one of R, R¹ and R² is other than H which comprises cyclizing a compound of the formula:

$$(R^2—NHC(=O)—CH_2—S)_2—CRR^1$$

in an aprotic reaction medium in the presence of a Hg$^{+2}$ metal catalyst.

2. The process of claim 1 wherein
R is H;
R¹ is

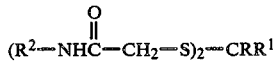

and
R² is

 or —(CH₂)₂—CH(OH)—(CH₂)$_{3-7}$—CH₃.

3. The process of claim 1 wherein:
R is phenyl,

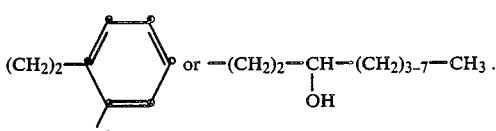

C₁-C₆ alkyl or —(CH₂)₅—COOH
R¹ is H or C₁-C₆ alkyl and
R² is H or C$_{1-4}$ alkylene 4. The process of claim 3 wherein:
R is phenyl, —(CH$_2$)$_4$—CH$_3$, 
CH$_2$CH(CH$_3$)$_2$—(CH$_2$)$_3$ 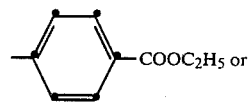
R$^1$ is H or CH$_3$ and
R$^2$ is H,
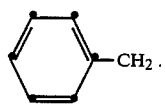
5. The process of claim 3 wherein:
R is (CH$_2$)$_5$—COOH and
R$^1$ and R$^2$ are each H.
* * * * *